United States Patent [19]

Merk

[11] Patent Number: 5,672,507
[45] Date of Patent: Sep. 30, 1997

[54] APPARATUS FOR THE SURFACE CULTURE OF NUCLEATED CELLS AND CELL CULTURE DEPENDENT SUBSTANCES

[75] Inventor: Walter Merk, Biberach an der Riss, Germany

[73] Assignee: Boehringer Ingelheim Animal Health, Inc., St. Joseph, Mo.

[21] Appl. No.: 393,742

[22] Filed: Feb. 24, 1995

Related U.S. Application Data

[63] Continuation-in-part of Ser. No. 259,206, Jun. 13, 1994, abandoned, which is a continuation of Ser. No. 110,283, Aug. 23, 1993, abandoned, which is a continuation of Ser. No. 986,840, Dec. 8, 1992, abandoned, which is a continuation of Ser. No. 648,092, Jan. 31, 1991, abandoned.

[51] Int. Cl.$^6$ .................................................. C12M 3/00
[52] U.S. Cl. ..................................... 435/295.2; 435/295.3
[58] Field of Search ........................ 435/240.23, 240.24, 435/240.46, 295.1, 295.2, 295.3

[56] References Cited

U.S. PATENT DOCUMENTS

| | | | |
|---|---|---|---|
| 3,957,585 | 5/1976 | Malick | 435/295.2 |
| 4,960,706 | 10/1990 | Bliem et al. | 435/295.3 |
| 5,256,580 | 10/1993 | Mulder et al. | 422/231 |
| 5,393,668 | 2/1995 | Cinatl et al. | 495/240.23 |

FOREIGN PATENT DOCUMENTS

| | | |
|---|---|---|
| 3164879 | 12/1986 | Japan . |
| 1160476 | 12/1987 | Japan . |

*Primary Examiner*—David A. Redding
*Attorney, Agent, or Firm*—R. P. Raymond; M-E. M. Devlin; A. R. Stempel

[57] ABSTRACT

An improved bio-reactor with spiral or coil-shaped filling bodies is disclosed, the improvement comprising use of a gas diffusion tube through which air, oxygen or other gases can be bubbled through the fermentation medium.

2 Claims, 1 Drawing Sheet

APPARATUS FOR THE SURFACE CULTURE OF NUCLEATED CELLS AND CELL CULTURE DEPENDENT SUBSTANCES

This is a continuation-in-part of application Ser. No. 08/259,206, filed Jun. 13, 1994 (abandoned), which is a continuation of application Ser. No., 08/110,283, filed Aug. 23, 1993 (abandoned), which is a continuation of application Ser. No., 07/986,840, filed Dec. 8, 1992 (abandoned), which is a continuation of application Ser. No., 07/648,092, filed Jan. 31, 1991 (abandoned).

In the EP-A-0,021,257 is described the surface culture of non-transformed nucleated cells and the production of cell culture-dependent substances from the cell thus obtained, there being used as culture face the surface of filling bodies hold which after the release of the medium back less than 8% of the medium relative to the free volume due to their form.

It is appropriate, when carrying out this process to use for the circulation of the medium a pump with which no shearing arise, such as for example, hose pumps. However, the agitation and aeration of nutrient medium is not optimal in the process as described by EP-A-0,021,257.

Surprisingly, it was found that the above-described disadvantages in surface culture and, therefore, in the production of cell culture-dependent substances such as interferon, viruses, enzymes, and immune antibodies such as, for example, immunoglobulins, can be eliminated if surface culture bodies can be used or selected which due to their form produce no disturbing inter facial effects, and thus permit complete covering and sufficient washing together with the concomitant use of a diffusion tube for the supply of air at the bottom of the culture vessel.

According to the invention there is provided an apparatus for surface-culture of nucleated cells comprising a vessel for surfaces of which cells grow during cultivation and an air diffusion tube arranged so that in use of the apparatus air is introduced at the bottom of the vessel and diffuses through the nutrient medium so as to allow the air to oxygenate the nutrient medium and cause the medium to circulate through the filling bodies, but preferably without air bubbles coming into contact with the filing bodies.

Preferably the air is introduced at a rate of five to twenty times volume of nutrient medium per hour, more preferably at the rate of ten times volume of nutrient medium per hour.

In a preferred embodiment the filling bodies are stainless steel wire spirals, expanded form, with a length of about 6 mm, width about 6 mm, a wire diameter of about 0,6 mm and a pitch of about 0,3 mm.

Useful filling bodies would be those which have a surface favorable for cell culture and offer the cells a sufficient possibility of adhesion and which, after the release of the medium, hold back less than 8% of the medium relative to free volume.

It has been now determined that such suitable filling bodies include fixed bodies such as floors and screens used in chemistry in fractionation distillation for the production of an optimal area for phase contact and moving bodies such as saddle-shaped bodies and spherical or cylindrical filling bodies, which can be made form materials such as glass; ceramic, for example, clay or porcelain; plastics, for example, Duramit®, a copolymer comprised of 10% butadiene and 90% styrene, available from Chem. Werke Hüls AG, Azidur, or Teflon®, tetrafluoroethylene fluorocarbon polymers available from E. I. duPont de Nemours + Co.; metals, for example titanium or stainless steel; or sintered products for example, corundum.

The term "moving filling bodies" encompasses rings such as Pall rings, Raschig rings, Prym rings, porcelain rings, Perfo rings, expanded metal rings, and Intos rings; coils and spirals such as glass spirals, Wilson spirals, spring coils, glass coils, wire spirals, spools and rolls; saddle-shaped bodies such as bead saddles, Super saddles, and Novalox saddles; Interlox and Interpack filling bodies, beads; balls; star-type filling bodies; twin bodies; and solid bodies; all of which are known in chemical fractional distillation.

Especially preferred filling bodies are, however, spirals, coils, and saddle-shaped bodies, particularly coils and wire spirals in expanded form made of stainless steel, in which the individual turns do not touch one another, or saddles, since these have simultaneously a large surface to the circulating medium and only a small flow resistance, so that during washing only a small amount of material is retained. Especially suitable are wire spirals which have a total average length of from about 4 to 8 mm, preferably from about 5 to 7 mm, a total width of from about 4 to 8 mm, and total wire diameter of from about 0.4 to 0.8 mm, the gap between the individual turns being from about 0.1 to 0.5 mm.

For example, the following filling bodies were tested for their suitability in the process according to the invention:

A - Glass rods (diameter: 10 mm, length: 30 mm);

B = Teflon® rings (outside diameter: 10.5 mm, inside diameter: 5.5 mm, length: 10.2 mm);

C = Duranit® cylinders (outside diameter: 10.5 mm, inside diameter: 6.5 mm, length: 11.5 mm);

D = Stainless steel spirals (outside diameter: 6 mm, wire diameter: 0.6 mm, length: 6 mm);

E = Glass balls (diameter: 10 mm);

F = Duranit® cylinders (outside diameter: 8 mm, inside diameter: 5 mm, length: 9.5 mm);

G = Glass rods (diameter: 6 mm, length: 10 mm);

H - Saddles (diameter: 6 MM, length: 6 mm);

I = Stainless steel wire gauze cylinders (diameter: 3 mm, length: 5 mm); and

K = Glass balls (diameter 3.5 to 5 mm) in comparison with

L = Glass cylinders (outside diameters: 4 mm, inside diameter: 2 mm, length: 6 mm).

Method

1. A glass test tube (inside diameter: 3 to 5 cm) was tapered downwardly to a funnel, fitted with a tube with an inside diameter of about 0.5 cm as outlet, and provided with a cock. A marking was made at the transition from the funnel to the 0.5 cm tube. With the cock closed the glass tube was then filled with water up to the mark, and the volume was determined by weighing the quantity drained, i.e., the output. It was subsequently filled up again with water to the mark, and a weighed quantity of water (for example, 200 ml) was added. The upper level was provided with a second marking. The water was then drained off down to the first mark. The remaining quantity of water which adhered to the glass wall was simultaneously determined by weighting the drained quantity and subtracting that weight from the weight of the fixed nominal volume. The entire operation was repeated several times and the average value was fixed as the value when empty.

Before each test the glass tube was completely dried (for example, by washing with acetone and subsequent blowing with air). The filling bodies to be tested were likewise dried in a drying chamber. For testing, the filling bodies were filled into the glass tube to the upper mark. The weight of the filling bodies introduced and the quantity were determined. Subsequently, with the cock closed a quantity of water from a previously weighed quantity was filled to the second mark, the filling quantity being determined by weighing the remainder quantity and subtracting that weight from the total weight of the previously weighed quantity. The filling quantity was fixed as the "free volume". The cock was subsequently opened and water running down to the first mark was weighed on a balance after collection in a tared vessel. By subtracting the drained quantity from the "free volume", the "remaining quantity" of water left in the filling bodies was calculated. The value when empty was taken into consideration. The surface of the filling bodies was either calculated or taken from the manufacturer's specifications.

The experimentally determined data was calculated for the following values: free volume per liter in $cm^3$, ratio of the surface of the filling bodies to the free volume, and remaining quantity after draining as a percent of the free volume.

2. With the same glass tube (dry), the same quantity of filling bodies was introduced and topped with dyed water (for example, 1% neutral red in water). The upper opening was then closed in an air-tight manner with a hose which was filled with water and clamped by a hose pump. After the cock had been opened, water was added via the hose pump in a measured quantity of 100 ml per minute, and the washing effect per minute was determined by measuring the color intensity in a photometer, with 1% neutral red in the water as 100%. The measured value was related to the initial value and calculated as washing effect in percent of residual dye after washing "x" times with a free volume quantity. Five minutes after the start of washing the intake of water was stopped, the volume was shaken briefly, and the value after 30 seconds of pumping was measured. The value is given as residual dye in a percentage after washing "x" times with a free volume quantity after subsequent shaking.

The results from the above procedures are set forth in the following table:

(2) have, after washing four times with a free volume quantity, a residual dye of a maximum of about 0.5% or, after washing four times with a free volume quantity, a residual dye of a maximum of about 0.5%.

Such filling bodies enable suspended nucleated cells, for example, fibroblast cells or epithelial cells, to adhere within a short time, for example, in one to three hours. Furthermore, the nutrients of the circulating medium are absorbed well, so that a rapid growth of the cells is ensured. However, it is especially advantageous that the closely grown cultures are brought in contact with induction substances within such time period and that the necessary removal of the induction substances by simple washing subsequently presents no great difficulties. Washing can be effected continuously or intermittently, that is, by replacing the circulating medium with a washing medium or by optionally draining off the medium several times and subsequently filling up with a washing or cleansing fluid. In the latter case, the washing or cleansing fluid is preferably introduced from the bottom.

Furthermore, the used filling bodies can be cleaned without difficulty and subsequently used again. This means, however, that on the one hand, the cells adhere sufficiently to the surface of such filling bodies to ensure undisturbed growth, but that they don't adhere so firmly that the cells cannot be detached upon subsequent cleaning.

The particular filling bodies are those which, after the release of the medium, hold back less than about 8% of the medium relative to free volume, that is, have a content due to adhesion smaller than about 8%, and thus possess no disturbing physical properties, for example, no disturbing interspacial effects (such as wetting or capillary action). It is appropriate that for the circulation of the medium, pumps are used with which no substantial shearing forces arise, such as, for example, hose pumps.

Expecially preferred filling bodies are those with which the ratio of surface of filling bodies to free volume is from about 20:1 to 2:1, preferably from about 15:1 to 5:1, and are made from stainless steel.

BRIEF DESCRIPTION OF THE DRAWINGS

The attached drawing.

TABLE 1

Figure 1:
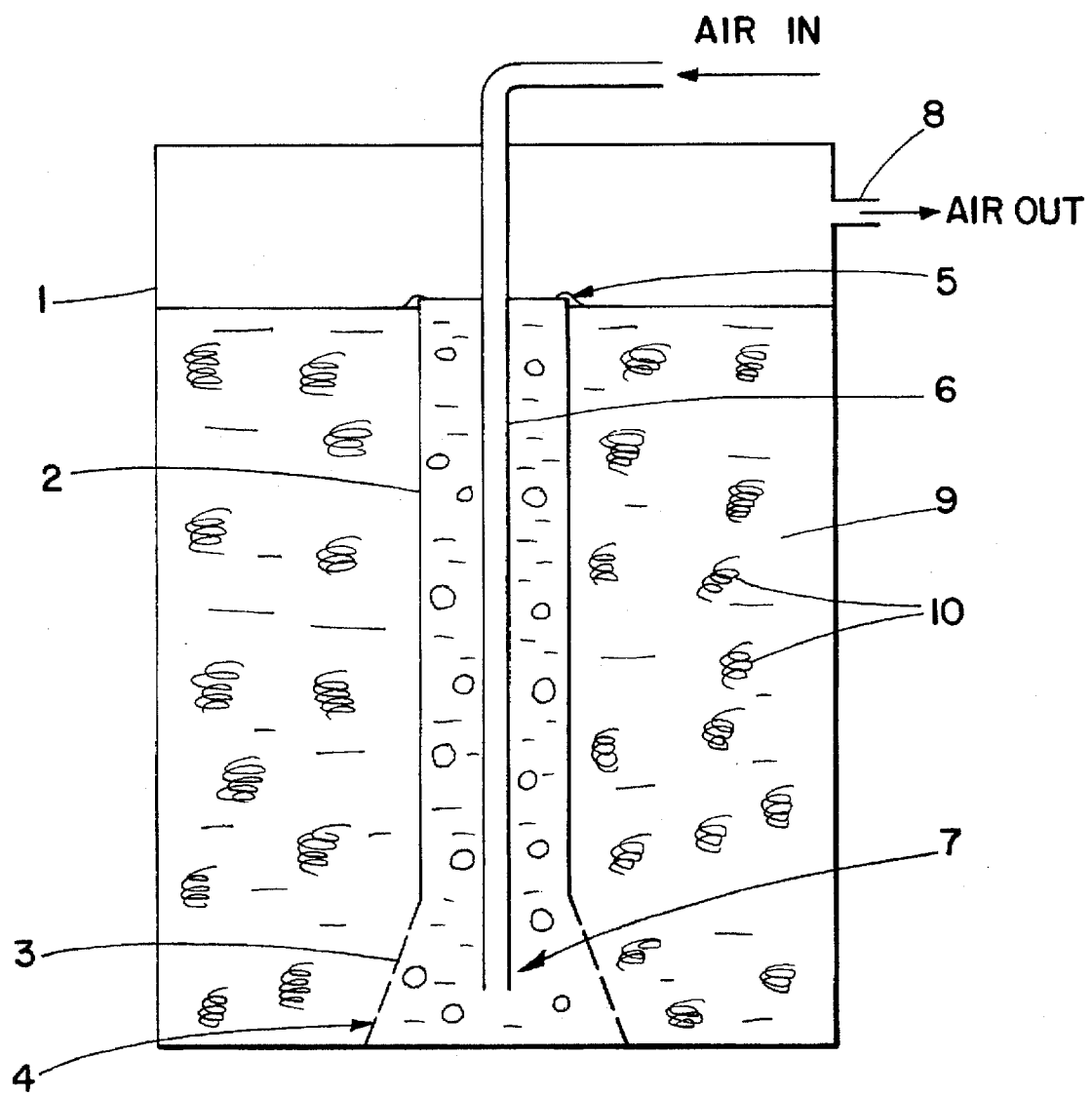
FIG. 1, shows an apparatus for surface-culture of nucleated cells according to the present invention.

| Filling Body | Free Volume per Liter ($cm^3$) | Ratio of Surface of Filling Bodies to Free Volume ($cm^2$:$cm^3$) | Residual Quantity After Draining (% of Free Volume) | Washing Effect after Washing with Free Volume Quantity (%) | | | Residual Dye | |
|---|---|---|---|---|---|---|---|---|
| | | | | Twice | 3 Times | 4 Times | % | Time Washed With Free Volume |
| A | 507 | 5.19:1 | 1.3 | 1.9 | 0.48 | 0.14 | 0.09 | 4.3 |
| B | 595 | 7.4:1 | 1.43 | 1.87 | 0.24 | 0.08 | 0.24 | 3.7 |
| C | 684 | 6.25:1 | 2.79 | 2.3 | 0.5 | 0* | 0.46 | 3.5 |
| D | 856 | 10.9:1 | 3.05 | 0.26 | 0 | 0 | 0 | 3 |
| E | 452 | 7.65:1 | 4.67 | 1.3 | 0.22 | 0.06 | 0.02 | 4.7 |
| F | 627 | 8.37:1 | 4.67 | 1.27 | 0.15 | 0* | 0.09 | 3.5 |
| G | 364 | 14.5:1 | 6.51 | 2.74 | 0.18 | 0.05 | 0.074 | 5.4 |
| H | 622 | 15.4:1 | 6.68 | 0.91 | 0.22 | 0 | 0 | 3.6 |
| I | 940 | 21.4:1 | 4.68 | 0.02 | 0 | 0 | 0 | 2.5 |
| K | 373 | 24.8:1 | 7.53 | 1.63 | 0.08 | 0.04 | 0.15 | 5.6 |
| L | 532 | 21.4:1 | 8.95 | 0.99 | 0.37 | 0.18 | 1.25 | 4.1 |

*Value determined graphically, the value to the left being the last experimental value.

Based on the above results, it can be seen that filling bodies suitable for the process according to the invention are those which:

(1) after the release of the medium hold back less than about 8% of medium relative to free volume (content due to adhesion), and The object of this invention is therefore an apparatus for surface-culture of nucleated cells comprising a vessel (1) for holding nutrient medium and containing filling bodies (10) on the surfaces of which cells grow during cultivation wherein the filling bodies (10) are located in a culture chamber (9) surrounding the tube (2), the tube (2)

extends from the bottom of the culture chamber (9) to an open end (5) at the top of the filled portion of the culture chamber (9) and has perforations (4) admitting of nutrient medium from the culture chamber (9) and an air diffusion tube (6) arranged so that in use of the apparatus air is introduced at the bottom of the vessel of an inlet of air (7) into the tube (2) and diffuses through the nutrient medium so as to allow the air to oxygenate the nutrient medium and causes the medium to circulate through the filling bodies, but preferably without coming into contact with the filling bodies.

A preferred embodiment of the invention is an apparatus for surface-culture of nucleated cells comprising a vessel (1) for holding nutrient medium containing filling bodies (10) up to a level proximate the upper end (5) of the tube (2), a tube (2) containing an air inlet diffusion tube (6), which passes from the outside of the vessel (1) and ends with its outlet (7) close to the bottom of the tube (2), whereby the tube (2) together with the air inlet diffusion tube (6) are so arranged that in use of the apparatus air is introduced at the bottom of the vessel (1) by the outlet (7) and the resulting air bubbles pass up through the annular space between the outer wall of the tube (6) and the inner wall of the tube (2) to allow the passed air to oxygenate the nutrient medium and to circulate the medium through the filling bodies, especially, an apparatus as hereinbefore described wherein the tubes (2) and (6) are located vertically and substantially centrally and the tube (2) has at its lower end the form of a skirt (3), which is perforated with holes (4) allowing to circulate the medium through the filling bodies.

The used filling bodies are those as hereinbefore defined.

A further object of the present invention is a method of cultivation nucleated cells wherein the cells are grown on filling bodies (10) wherein the filling bodies (10) are located in a culture chamber (9) surrounding the tube (2), the tube (2) extends from the bottom of the culture chamber (9) to an open end (5) at the top of the filled portion of the culture chamber (9) and has perforations (4) admitting of nutrient medium from the culture chamber (9)

in a vessel (1) holding nutrient medium and air is introduced through a diffusion tube (6) at the bottom of the vessel by an inlet of air (7) and is bubbled through the nutrient medium so as to allow to oxygenate the nutrient medium and cause the medium to circulate through the filling bodies (10), but preferable without air bubbles coming into contact with the filling bodies which are as hereinbefore defined, whereby the air is introduced at a rate of five to twenty times, preferably at a rate of ten times the volume of nutrient medium per hour. The cells growing on the surface of the filling bodies used are for example infected with a virus of predetermined identity to prepare the derived culture dependend compound, whereby the culture medium may be removed from the vessel (1) after a predetermined period of time.

The resulting air bubbles pass up through the annular space between the outer wall of tube (6) and inner wall of tube (2), drawing nutrient medium with them. The nutrient medium is thus drawn from culture chamber (9) through holes (4) and upwards through the aforesaid annular space; it then overflows at the upper end (5) of the tube (2) and reenters the culture chamber (9). Air is withdrawn via outlet (8).

The simultaneous oxygenation and circulation of the culture medium is thus achieved with great simplicity and economy.

The following examples are intended to illustrate the invention and are not to be construed as limiting the invention thereto.

REFERENCE EXAMPLE I

A 25 liter double-jacket reaction vessel of Duran glass was filled with 17 liters of carefully washed filling bodies stainless steel wire spirals, expanded form, length about 6 mm, width about 6 mm, wire diameter about 0,6 mm, pitch about 0,3 mm (ratio of surface of filling bodies to free volume was about 11:1). The inlet and outlet were provided with silicon rubber hoses, inside diameter 8 to 10 mm, and were carried via pH electrodes with a pH meter and permeator and connected to the circuit. The apparatus was sterilized with superheated steam. Cells obtained by trypsination of surface cell cultures were suspended in 17 liters of minimum essential medium with 10% fetal calf serum and 200 µg/ml of kanamycin in a quantity of 20,000 cells/cm$^2$, and were introduced into the reaction vessel. The reaction vessel was heated to 37° C. via the double jacket, and was maintained at such temperature. The cell culture suspension was left for about two to four hours in the reaction vessel without pumped circulation. Subsequently, a silicone hose was inserted into a hose pump and circulation was effected at a rate of 30 revolutions per minute with a delivery rate of about 40 to 80 liters per hour. The pH value was adjusted to between 7.3 and 7.5. Twenty-four to forty-eight hours after the starting point, medium was removed at regular intervals and fresh, growth medium of the same composition was added. Altogether, about 80 liters of medium were added and removed over the following three to four days. Eight to ten days after introduction of the cell culture the entire medium was removed and the cells were washed by the addition of minimum essential medium without serum, and the induction medium, which contained 100 µg/ml of Poly I:C and 2.5 µg/ml of cycloheximide, was subsequently added thereto. The medium was left for three hours in the reaction vessel. About 2 µg/ml of actinomycin D was subsequently added. One hour after the addition of the actinomycin D, the entire induction medium was removed and the cells were washed at least four times with minimum essential medium without serum. Subsequently, minimum essential medium containing 1,000 µg/ml of serum albumin was added, the circulated by pumping, as described above. The pH value was adjusted to 7.5 to 7.6. Nineteen to twenty hours later the medium was harvested, and was concentrated and purified by known processes.

The yields of interferon in the crude solution were about 900 to 2,000 units/cm$^2$ of culture face, as determined according to the International Reference Preparation B 023-902-527 of the National Institute of Health, USA.

With the use of various filling bodies in different starting quantities, fibroblast interferon was prepared in analogous manner with the results set forth in the following table:

TABLE 2

| Filling Bodies | Starting Quantity (liters) | Interferon Reference Units per cm$^2$ of Culture Face |
| --- | --- | --- |
| A | 0.2 | 1,147 |
| A | 0.2 | 1,956 |
| A | 1.2 | 593 |
| B | 0.3 | 83 |
| D | 2.2 | 1,580 |
| D | 17.0 | 1,374 |

TABLE 2-continued

| Filling Bodies | Starting Quantity (liters) | Interferon Reference Units per $cm^2$ of Culture Face |
|---|---|---|
| D | 108.0 | 1,103 |
| H | 0.2 | 470 |
| L | 0.2 | 23 |
| L | 0.2 | 19 |

As described below, in the practice of the present invention there is used of a diffusion tube preferably in the center of the container holding the cells and nutrient medium. The filling bodies surround such diffusion tube. Air is introduced through the diffusion tube at an opening(s) near the bottom of the container holding the cells and nutrient medium. The air flow from such diffusion tube diffuses through the cells and nutrients, preferably at an approximate rate of about five to twenty, more preferably ten, times the volume of the reaction medium per hour providing gentle agitation and also oxygenation of the nutrient medium.

EXAMPLE I

Use of the diffusion tube presents unexpected advantages. For example, a production trial with bovine diarrhea virus was run using a container with a diffusion tube substantially as described in FIG. 1 and one without such tube. A bovine kidney cell line was inoculated into the growth container, which has previously been loaded with coil-shaped filling bodies (as described in Example 1) to enable attachment of such cells to the coils for growth and multiplication. The nutrient medium used as DMF+10% fetal bovine serum, pH 7.0. Air was sparged into the growth vessels to maintain a constant supply of nutrients and oxygen flowing over the cells.

On day 8, the growth medium was removed, and seed medium, MEM/LH+2% horse serum, pH 7.6, was introduced to the growth vessel. BVD virus was then seeded into the growth vessel. Again, air was sparged into the growth vessel.

On day 11 and day 14, the growth vessels were harvested by removing the fluid medium. Samples of this medium were taken for potency assay. The results were:

| | Vessel with Diffusion Tube | Vessel Without Diffusion Tube |
|---|---|---|
| Harvest 1 (Day 11) | $10^{6.4}$ $TCID_{50}$/ml | $10^{5.5}$ $TCID_{50}$/ml |
| Harvest 2 (Day 14) | $10^{6.5}$ $TCID_{50}$/ml | $10^{6.4}$ $TCID_{50}$/ml |

As is apparent, a higher titer (by ten-fold) was obtained on the first harvest. Accordingly the use of the diffusion tube will result in both a higher yield for any, given production run and longer production process, i.e., less time is spent in getting the growth vessel to production and harvesting. It appears that by use of the diffusion tube there is less "channeling" of air bubbles. Accordingly, the coils used as the support for cell growth are more uniformly agitated.

Whilst the above description describes a diffusion system using air it is to be understood that in order to optimise the pH, $PO_2$ in the culture medium and other operating parameters the diffusion gas may be supplemented with e.g. oxygen, carbondioxide and nitrogen.

The preceding specific embodiments are illustrative of the practice of the invention. It is to be understood, however, that other expedients known to those skilled in the art or disclosed herein, may be employed without departing from the scope of the appended claims.

What is claimed is:

1. An apparatus for surface-culture of nucleated cells comprising:

(a) a vessel for holding nutrient medium and filling bodies on the surfaces of which filling bodies nucleated cells grow during cultivation;

(b) a cylindrical culture chamber disposed centrally along the vertical axis of the vessel which chamber holds the nutrient medium and filling bodies within the vessel such that the nutrient medium and filling bodies substantially fill the culture chamber but leaving a space at the top of the culture chamber;

(c) a tube located along the center, vertical axis of the culture chamber having a bottom skirt-like projection, which skirt-like projection is attached to the bottom of the culture chamber and the top of the tube extends towards the top of the culture chamber so as to meet and slightly exceed the level of nutrient medium and filling bodies within the culture chamber, and the surface walls of the tube are perforated so as to allow nutrient medium to pass through but not to allow filling bodies to pass through from the culture chamber, and (d) an air diffusion tube disposed along the center vertical axis of the tube having an outlet opening and an inlet opening so that air can be introduced at the bottom of the tube through its outlet opening and then the air can diffuse through the nutrient medium within the tube to oxygenate such nutrient medium and cause the oxygenated nutrient medium to pass through the perforations in the surface walls of the tube and around the filing bodies in the culture chamber, which air diffusion tube's inlet opening is outside of the vessel and its outlet opening is close to the bottom of the tube, whereby the tube together with the air diffusion tube are so arranged that in use air is introduced at the bottom of the culture chamber through the outlet opening of the air diffusion tube and the resulting air bubbles pass up through the annular space between the tube and the air diffusion of the tube to allow the passed air to oxygenate the nutrient medium and to circulate the medium through the filling bodies.

2. The apparatus as recited in claim 1 wherein the perforations on the surface walls of the tube are located only on the skirt-like projection of the tube.

* * * * *